US00PP29929P3

(12) United States Plant Patent
Olesen

(10) Patent No.: US PP29,929 P3
(45) Date of Patent: Dec. 4, 2018

(54) MINIATURE ROSE PLANT NAMED 'POULTY021'

(50) Latin Name: ***Rosa* hybrid**
Varietal Denomination: Poulty021

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 53 days.

(21) Appl. No.: 15/330,286

(22) Filed: Sep. 6, 2016

(65) Prior Publication Data

US 2018/0070498 P1 Mar. 8, 2018

(51) Int. Cl.
*A01H 5/02* (2018.01)
*A01H 6/74* (2018.01)

(52) U.S. Cl.
USPC ..... Plt./119
CPC ..... *A01H 5/02* (2013.01); *A01H 6/749* (2018.05)

(58) Field of Classification Search
USPC ..... Plt./119
See application file for complete search history.

(56) References Cited

PUBLICATIONS

Perfection by Poulsen, Oct. 2013.*

* cited by examiner

*Primary Examiner* — Keith O. Robinson

(57) ABSTRACT

A new garden rose plant of the Miniature class which has abundant, orange blend flowers and attractive foliage. This new and distinct variety has shown to be uniform and stable in the resulting generations from asexual propagation.

2 Drawing Sheets

Botanical designation: *Rosa* hybrid.
Variety denomination: 'Poulty021'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2009 and the resulting seeds were planted in a controlled environment in Fredensborg, Denmark. The new variety, named 'Poulty021', originated as a single seedling from the stated cross.

The new variety may be distinguished from its male pollen parent and female seed parent primarily by the following characteristics. The female seed parent has orange red flowers while the new variety has orange blend flowers. The male pollen parent has red flowers while the new variety has orange blend flowers.

The objective of the hybridization of this rose variety was to create a new and distinct variety with unique qualities, such as:

1. Uniform and abundant orange blend flowers;
2. Vigorous, but compact growth when propagated on its own roots;
3. Exceptional disease resistance.

This combination of qualities is not present in previously available commercial cultivars of this type, known to the inventor, and distinguish 'Poulty021' from all other varieties of which we are aware.

As part of the rose development program, Mogens N. Olesen germinated the seeds from the aforementioned hybridization during winter of 2009 and conducted evaluations on the resulting seedlings in a controlled environment in Fredensborg, Denmark. 'Poulty021' was selected in the spring of 2010 by the inventor as a single plant from the progeny of the aforementioned hybridization.

Asexual reproduction of 'Poulty021' by rooted cuttings was first done by Mogens N. Olesen in the nursery in Fredensborg, Denmark in July, 2010. This initial and other subsequent asexual propagations conducted in controlled environments have demonstrated that the characteristics of 'Poulty021' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty021'.

Specifically illustrated in one of the drawings are open flower viewed from above, flower petals detached, sepals detached showing receptacle and reproductive flower parts, leaves, and a flowering branch with many unopened flower buds.

The other drawing shows the entire plant flowering in a container. Plants shown are 2 years of age.

DETAILED DESCRIPTION OF THE VARIETY

The following is a description of 'Poulty021', as observed in its growth in a field nursery in Marion County, Oreg.

Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar071', U.S. Plant Pat. No. 24,549 are compared to 'Poulty021' in Chart 1.

CHART 1

| | 'Poulty021' | 'Poulpar071' |
|---|---|---|
| Petal Count | 50 | 70 |
| Flower Diameter | 50 mm | 50 to 60 mm |
| General Tonality of Flower Color | Red Group 41C | Orange Red Group 32B |

Flower and flower bud:

*Blooming habit*.—Continuous.

*Flower bud*.—Size: Upon opening, 10 mm in length from base of receptacle to end of bud. Bud diameter is 10 mm. Bud form: Ovoid. Sepal inner surface: Color: Yellow-Green Group 146D. Surface: Lightly pubescent. Sepal outer surface: Color: Yellow-Green Group 144A. Texture: Smooth. Sepal Shape: Apex: Cirrhose. Base: Flat at union with receptacle. Sepal Margin: Margins have moderate to strong foliaceous appendages on three of the five sepals. Sepal size: 18 mm long, 6 mm wide. Receptacle: Texture: Smooth. Size: 5 mm in height, 5 mm wide. Color: Yellow-Green Group 144A with strong intonations of Greyed-Orange Group 166A. Shape: Funnel. Pedicel: Surface: Smooth. Length: 20 mm. Diameter: 2 mm on average. Color: Greyed-Orange Group 176A. Strength: Strong. Peduncle: Length: 1 to 6 cm. Diameter: About 4 mm. Color: Yellow-Green Group 145A. Texture: Smooth.

*Flower bud development*.—Flower buds are borne in clusters of 5 to 9 flower buds per stem in the form of a panicle.

*Flower bloom*.—Fragrance: Strong perfume. Duration: The blooms have a duration on the plant of approximately 10 days. Petals fall cleanly away from plant after flowers have fully matured. Size: Flower diameter is 50 mm when open. Flower depth is 25 mm. Flower shape: Rosette double flower with many slightly overlapping petals of different sizes.

*Petalage*.—Under normal conditions, flowers have about 50 petals.

*General tonality of flower*.—Open flowers are Red Group 41C.

*Petal color*.—After opening, outer and inner petals Upper surface: Red Group 41C splashed with intonations Orange Group 29C. Lower surface: Red Group 43C. Basal petal spots, after opening: Upper surface: Yellow Group 5B, about 5 mm height by 5 mm wide. Lower surface: Yellow Group 5B, about 5 mm height by 5 mm wide.

*Petals*.—Petal Reflex: Slightly reflexed. Margin: Entire and uniform. Light undulations. Shape: Broad and elliptic. Apex shape: Rounded. Base shape: Rounded. Size: 24 mm (l)×26 mm (w). Texture: Smooth. Thickness: Average.

*Reproductive flower parts*.—Pollen: None observed. Anthers: Size: 1 mm in length. Color: Yellow Group 4C. Quantity: 25 on average. Filaments: Color: Red Group 41B. Length: 2 mm. Pistils: Length: 4 mm. Quantity: 17 on average. Stigmas: Color: Green-White Group 157A. Styles: Color: Green-White Group 157A. Location of stigmas: Superior in location relative to the length of the filaments and the height of the anthers. Hips: None Observed.

Plant:

*Plant growth*.—Upright, bushy. Plants are about 25 cm in height, and 25 cm wide.

*Stems*.—Color of juvenile growth: Yellow-Green Group 144B. Color of mature growth: Yellow-Green Group 144A. Length: Canes are about 11 cm from the base of the plant to the flowering portion. Diameter: About 4 mm. Internodes: On mature canes about 22 mm between nodes. Surface Texture: Young wood: Smooth. Older wood: Smooth.

*Long prickles*.—Incidence: 4 prickles per 10 cm of stem. Size: Average length of prickles on mature stems is 3 mm. Shape: Upper portion is linear. Lower portion is concave. Color: Juvenile prickles: Greyed-Red Group 181B. Mature prickles: Greyed-Red Group 181B.

*Plant foliage*.—Compound leaf: 50 mm (l)×35 (w). Quantity: About 3 leaves per 10 cm of stem on average. Leaf bearing angle to the stem: 60 degrees. Color of juvenile foliage: Upper side: Yellow-Green Group 144A. Lower side: Yellow-Green Group 144B. Color of mature foliage: Upper side: Yellow-Green Group 146A with intonations of Greyed-Purple Group 187A on margins. Lower side: Yellow-Green Group 147C.

*Plant leaves and leaflets*.—Stipules: Size: 10 mm long, 3 mm wide. Quantity: 2 per compound leaf. Shape: Linear, slightly broad based with outward extending apices. Margins: Finely serrated. Color: Yellow-Green Group 144A. Petiole: Length: 15 mm. Diameter: About 1.5 mm. Upper surface color: Yellow-Green Group 144A with intonations of Greyed-Purple Group 187A. Lower surface color: Yellow-Green Group 144A. Rachis: Length: About 18 mm Upper surface color: Yellow-Green Group 144A with intonations of Greyed-Purple Group 187A. Lower surface color: Yellow-Green Group 144A. Leaflet: Quantity: Normally 5 leaflets. Margins: Serrated. Size: Terminal leaflets are about 20 mm long, 15 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

*Disease resistance*.—Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

*Cold hardiness*.—The variety is tolerant to USDA Cold Hardiness Zone 6.

*Heat tolerance*.—The variety has been found to be suitable for climate conditions found in the American Horticulture Society heat zone 7.

I claim:

1. A new and distinct variety of rose plant of the Miniature rose class named 'Poulty021', substantially as illustrated and described herein, due to its abundant orange blend flowers, disease resistance, and extended period of bloom.

* * * * *

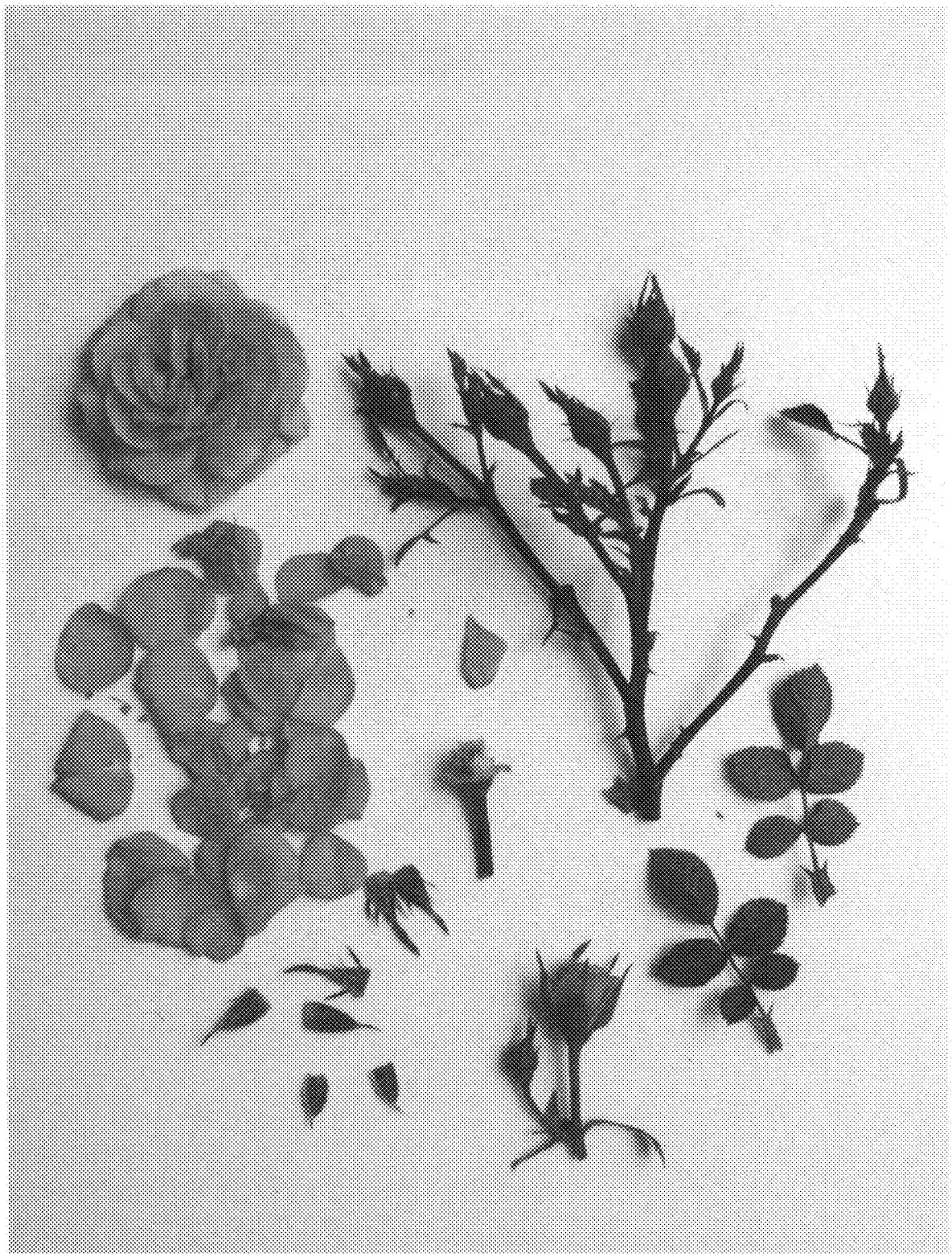

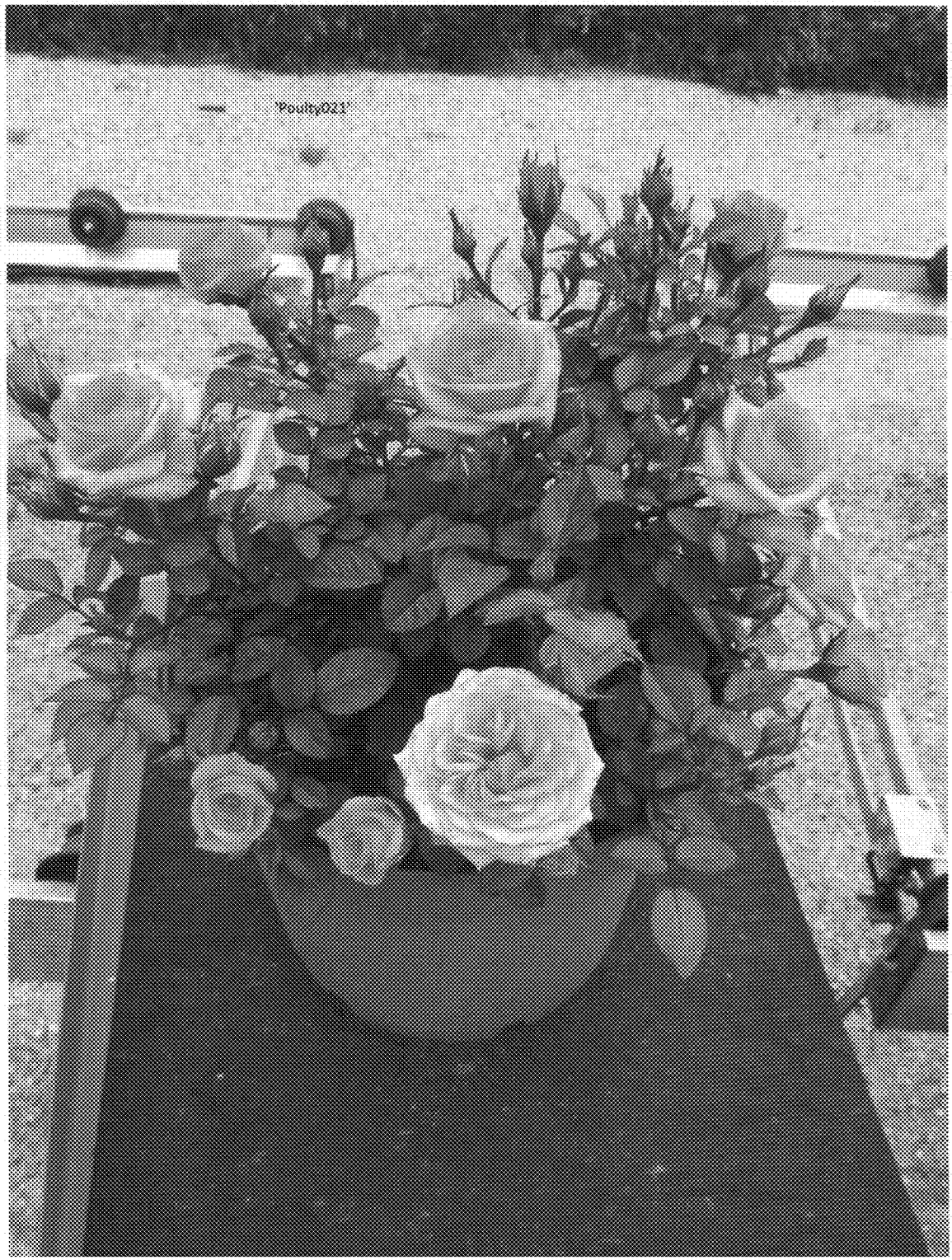
'Poulty023'